United States Patent
Mattmiller et al.

(10) Patent No.: US 9,504,516 B2
(45) Date of Patent: Nov. 29, 2016

(54) GAIN COMPENSATION FOR A FULL BRIDGE INVERTER

(71) Applicant: COVIDIEN LP, Mansfield, MA (US)

(72) Inventors: Aaron Mattmiller, Longmont, CO (US); Donald Tonn, Superior, CO (US); Alexander M. Waskiewicz, Boulder, CO (US)

(73) Assignee: COVIDIEN LLP, Mansfield, MA (US)

( * ) Notice: Subject to any disclaimer, the term of this patent is extended or adjusted under 35 U.S.C. 154(b) by 346 days.

(21) Appl. No.: 14/168,296

(22) Filed: Jan. 30, 2014

(65) Prior Publication Data
US 2014/0358138 A1 Dec. 4, 2014

Related U.S. Application Data

(60) Provisional application No. 61/829,433, filed on May 31, 2013.

(51) Int. Cl.
*A61B 18/12* (2006.01)
*A61B 18/00* (2006.01)

(52) U.S. Cl.
CPC .... *A61B 18/1206* (2013.01); *A61B 2018/0075* (2013.01); *A61B 2018/00702* (2013.01); *A61B 2018/00726* (2013.01); *A61B 2018/00827* (2013.01); *A61B 2018/00875* (2013.01); *A61B 2018/00892* (2013.01); *A61B 2018/1286* (2013.01)

(58) Field of Classification Search
CPC ............... A61B 18/1206; A61B 2018/00636; A61B 2018/0075; A61B 2018/00779; A61B 2018/00827; A61B 2018/00875; A61B 2018/00892; A61B 2018/00773
See application file for complete search history.

(56) References Cited

U.S. PATENT DOCUMENTS

| 3,601,126 A | 8/1971 | Estes |
| 3,683,923 A | 8/1972 | Anderson |
| 3,826,263 A | 7/1974 | Cage et al. |

(Continued)

FOREIGN PATENT DOCUMENTS

| DE | 179607 C | 3/1905 |
| DE | 390937 C | 3/1924 |

(Continued)

OTHER PUBLICATIONS

European Search Report No. 14166165.2 dated Jul. 8, 2014.

(Continued)

*Primary Examiner* — Jaymi Della

(57) ABSTRACT

An electrosurgical generator and related systems and methods using a gain-compensated full bridge topology. Gain nonlinearity is corrected by applying impedance and phase correction factors to a control loop to achieve a linear gain structure. In embodiments, gain compensation is performed by comparing an RF setpoint signal with a calculated output signal to generate a first error signal. An impedance correction factor is applied to the first error signal to generate a second error signal. The second error signal is processed by a proportional-integral-derivative controller to generate a phase control signal. A phase control correction factor is applied to the phase control signal to generate a corrected pulse width modulation driving signal, which is used to generate PWM driving signals for a full-bridge inverter. One or more sensors provide feedback for comparison with the RF setpoint.

20 Claims, 10 Drawing Sheets

(56) References Cited

U.S. PATENT DOCUMENTS

| | | |
|---|---|---|
| 3,964,487 A | 6/1976 | Judson |
| 3,978,393 A | 8/1976 | Wisner et al. |
| 3,980,085 A | 9/1976 | Ikuno |
| 4,092,986 A | 6/1978 | Schneiderman |
| 4,126,137 A | 11/1978 | Archibald |
| 4,188,927 A | 2/1980 | Harris |
| 4,281,373 A | 7/1981 | Mabille |
| 4,287,557 A | 9/1981 | Brehse |
| 4,524,444 A | 6/1985 | Efron et al. |
| 4,586,120 A | 4/1986 | Malik et al. |
| 4,590,934 A | 5/1986 | Malis et al. |
| 4,658,819 A | 4/1987 | Harris et al. |
| 4,727,874 A | 3/1988 | Bowers et al. |
| 4,887,199 A | 12/1989 | Whittle |
| 4,961,047 A | 10/1990 | Carder |
| 5,099,840 A | 3/1992 | Goble et al. |
| 5,113,116 A | 5/1992 | Wilson |
| 5,216,338 A | 6/1993 | Wilson |
| 5,396,194 A | 3/1995 | Williamson et al. |
| 5,414,238 A | 5/1995 | Steigerwald et al. |
| 5,498,261 A | 3/1996 | Strul |
| 5,531,774 A | 7/1996 | Schulman et al. |
| 5,559,688 A | 9/1996 | Pringle |
| 5,678,568 A | 10/1997 | Uchikubo et al. |
| 5,702,386 A | 12/1997 | Stern et al. |
| 5,729,448 A | 3/1998 | Haynie et al. |
| 5,755,715 A | 5/1998 | Stern et al. |
| 5,906,614 A | 5/1999 | Stern et al. |
| 6,123,702 A | 9/2000 | Swanson et al. |
| 6,162,217 A | 12/2000 | Kannenberg et al. |
| 6,183,468 B1 | 2/2001 | Swanson et al. |
| 6,245,065 B1 | 6/2001 | Panescu et al. |
| 6,409,722 B1 | 6/2002 | Hoey et al. |
| 6,494,880 B1 | 12/2002 | Swanson et al. |
| 6,537,272 B2 | 3/2003 | Christopherson et al. |
| 6,693,782 B1 | 2/2004 | Lash |
| 6,696,844 B2 | 2/2004 | Wong et al. |
| 6,733,495 B1 | 5/2004 | Bek et al. |
| 6,736,810 B2 | 5/2004 | Hoey et al. |
| 6,740,079 B1 | 5/2004 | Eggers et al. |
| 6,740,085 B2 | 5/2004 | Hareyama et al. |
| 6,849,073 B2 | 2/2005 | Hoey et al. |
| 6,939,346 B2 | 9/2005 | Kannenberg et al. |
| 6,942,660 B2 | 9/2005 | Pantera et al. |
| 6,974,463 B2 | 12/2005 | Magers et al. |
| 7,041,096 B2 | 5/2006 | Malis et al. |
| 7,058,372 B1 | 6/2006 | Pardoen et al. |
| 7,062,331 B2 | 6/2006 | Zarinetchi et al. |
| 7,169,144 B2 | 1/2007 | Hoey et al. |
| 7,190,933 B2 | 3/2007 | De Ruijter et al. |
| 7,203,556 B2 | 4/2007 | Daners |
| 7,247,155 B2 | 7/2007 | Hoey et al. |
| 7,250,746 B2 | 7/2007 | Oswald et al. |
| 7,269,034 B2 | 9/2007 | Schlecht |
| 7,294,127 B2 | 11/2007 | Leung et al. |
| 7,396,336 B2 | 7/2008 | Orszulak et al. |
| D574,323 S | 8/2008 | Waaler |
| 7,468,499 B2 | 12/2008 | Canini et al. |
| 7,511,472 B1 | 3/2009 | Xia et al. |
| 7,582,084 B2 | 9/2009 | Swanson et al. |
| 7,655,003 B2 | 2/2010 | Lorang et al. |
| 7,722,601 B2 | 5/2010 | Wham et al. |
| 7,736,358 B2 | 6/2010 | Shores et al. |
| 7,799,020 B2 | 9/2010 | Shores et al. |
| 7,863,841 B2 | 1/2011 | Menegoli et al. |
| 8,012,150 B2 | 9/2011 | Wham et al. |
| 8,045,943 B2 | 10/2011 | Kaczman et al. |
| 8,080,008 B2 | 12/2011 | Wham et al. |
| 8,096,961 B2 | 1/2012 | Orszulak et al. |
| 8,113,057 B2 | 2/2012 | Orszulak et al. |
| 8,267,929 B2 | 9/2012 | Wham et al. |
| 8,287,529 B2 | 10/2012 | Orszulak |
| 8,298,223 B2 | 10/2012 | Wham et al. |
| 8,303,580 B2 | 11/2012 | Wham et al. |
| 8,377,053 B2 | 2/2013 | Orszulak |
| 8,485,993 B2 | 7/2013 | Orszulak et al. |
| 2003/0199863 A1 | 10/2003 | Swanson et al. |
| 2004/0172016 A1 | 9/2004 | Bek et al. |
| 2005/0004564 A1 | 1/2005 | Wham et al. |
| 2006/0161148 A1* | 7/2006 | Behnke .............. A61B 18/1206 606/34 |
| 2006/0224151 A1 | 10/2006 | Waaler |
| 2006/0293649 A1 | 12/2006 | Lorang et al. |
| 2007/0093800 A1 | 4/2007 | Wham et al. |
| 2007/0093801 A1 | 4/2007 | Behnke |
| 2008/0015563 A1 | 1/2008 | Hoey et al. |
| 2008/0015564 A1 | 1/2008 | Wham et al. |
| 2008/0082095 A1 | 4/2008 | Shores et al. |
| 2008/0082096 A1 | 4/2008 | Shores et al. |
| 2008/0287791 A1 | 11/2008 | Orszulak et al. |
| 2008/0287838 A1 | 11/2008 | Orszulak et al. |
| 2009/0030477 A1 | 1/2009 | Jarrard |
| 2010/0063494 A1 | 3/2010 | Orszulak |
| 2010/0063497 A1 | 3/2010 | Orszulak |
| 2010/0121318 A1 | 5/2010 | Hancock et al. |
| 2010/0168730 A1 | 7/2010 | Hancock et al. |
| 2010/0191233 A1 | 7/2010 | Wham et al. |
| 2010/0211063 A1 | 8/2010 | Wham et al. |
| 2010/0268220 A1 | 10/2010 | Johnson et al. |
| 2011/0068828 A1 | 3/2011 | Anderson et al. |
| 2011/0087213 A1 | 4/2011 | Messerly et al. |
| 2012/0089139 A1 | 4/2012 | Wham et al. |
| 2012/0116268 A1 | 5/2012 | Orszulak et al. |
| 2012/0239026 A1 | 9/2012 | Orszulak et al. |
| 2012/0265195 A1 | 10/2012 | Gilbert |
| 2013/0023869 A1 | 1/2013 | Orszulak |
| 2013/0035679 A1 | 2/2013 | Orszulak |
| 2013/0066311 A1 | 3/2013 | Smith et al. |
| 2013/0079763 A1 | 3/2013 | Heckel et al. |
| 2013/0158541 A1 | 6/2013 | Orszulak |
| 2013/0325380 A1 | 12/2013 | Behnke, II et al. |
| 2014/0039490 A1 | 2/2014 | Wham |
| 2014/0043070 A1 | 2/2014 | Gilbert |
| 2014/0058381 A1 | 2/2014 | Wham et al. |
| 2014/0058385 A1 | 2/2014 | Wham et al. |
| 2014/0062593 A1 | 3/2014 | Gilbert |
| 2014/0094796 A1 | 4/2014 | Behnke, II |
| 2014/0100559 A1 | 4/2014 | Wham et al. |
| 2014/0114303 A1 | 4/2014 | Johnston |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |

(56) References Cited

FOREIGN PATENT DOCUMENTS

| EP | 336742 A2 | 10/1989 |
|---|---|---|
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1263181 A1 | 12/2002 |
| EP | 1366724 A1 | 12/2003 |
| EP | 1681026 A2 | 7/2006 |
| EP | 1776929 A1 | 4/2007 |
| EP | 2393208 A2 | 12/2011 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 2164473 A | 3/1986 |
| GB | 2214430 A | 9/1989 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 02/11634 A1 | 2/2002 |
| WO | 0232333 A1 | 4/2002 |
| WO | 02/45589 A2 | 6/2002 |
| WO | 03/047446 A1 | 6/2003 |
| WO | 03/090635 A1 | 11/2003 |
| WO | 2004/098385 A2 | 11/2004 |
| WO | 2006/050888 A1 | 5/2006 |
| WO | 2008/043999 A2 | 4/2008 |
| WO | 2008/053532 A1 | 5/2008 |
| WO | 2008/071914 A2 | 6/2008 |
| WO | 2008/110756 A2 | 9/2008 |

OTHER PUBLICATIONS

Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. Ml, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 13/943,518 dated Jul. 16, 2013 inventor: Orszulak et al.
U.S. Appl. No. 14/069,534 dated Nov. 1, 2013 inventor: Digmann.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/183,196 dated Feb. 18, 2014 inventor: Krapohl.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/192,112 dated Feb. 27, 2014 inventor: Weinberg.
U.S. Appl. No. 14/255,051 dated Apr. 17, 2014 inventor: Coulson.
European Examination Report from EP Appl. No. 14166165.2 dated Apr. 21, 2016.

* cited by examiner

GAIN COMPENSATION FOR A FULL BRIDGE INVERTER

CROSS REFERENCE TO RELATED APPLICATION

The present application claims the benefit of and priority to U.S. Provisional Application Ser. No. 61/829,433, filed on May 31, 2013, the entire contents of which are incorporated herein by reference.

BACKGROUND

1. Technical Field

The present disclosure is directed to electrosurgical systems, and, in particular, to a circuit and method for achieving gain compensation across varying operating conditions in an electrosurgical generator utilizing a full bridge topology.

2. Description of the Related Art

An electrosurgical generator is used in surgical procedures to deliver electrical energy to the tissue of a patient. When an electrode is connected to the generator, the electrode can be used for cutting, coagulating or sealing the tissue of a patient with high frequency electrical energy. During normal operation, alternating electrical current from the generator flows between an active electrode and a return electrode by passing through the tissue and bodily fluids of a patient.

The electrical energy usually has its waveform shaped to enhance its ability to cut, coagulate or seal tissue. Different waveforms correspond to different modes of operation of the generator, and each mode gives the surgeon various operating advantages. Modes may include cut, coagulate, a blend thereof, desiccate, seal, or spray. A surgeon can easily select and change the different modes of operation as the surgical procedure progresses.

In each mode of operation, it is important to regulate the electrosurgical energy delivered to the patient to achieve the desired surgical effect. Applying more than the correct dosage may result in tissue destruction, and may prolong healing. Applying less than the desired dosage of energy power inhibits the surgical procedure. Thus, it is desirable to control the output energy from the electrosurgical generator for the type of tissue being treated.

Different types of tissues will be encountered as the surgical procedure progresses and each unique tissue requires more or less power as a function of frequently changing tissue impedance. As different types of tissue and bodily fluids are encountered, the impedance changes and the response time of the electrosurgical control of output power must be rapid enough to seamlessly permit the surgeon to treat the tissue. Moreover, the same tissue type can be desiccated during electrosurgical treatment and thus its impedance will change dramatically in the space of a very brief time. The electrosurgical output power control has to respond to such impedance changes as well.

Three standard modes of control are commonly used during electrosurgical generation. At low tissue impedances, the generator controls to a current limit. At mid-range tissue impedances, the generator controls to a power limit. At highest tissue impedances, the generator controls to a voltage limit. Generally, the voltage, current, and power limits describe the electrosurgical mode. The generator must employ a stable control loop over the full impedance range whether controlling to voltage, current, or power.

In prior-art electrosurgical generator designs, voltage from the AC mains is rectified to provide a DC voltage. An inverter stage converts the DC voltage back to AC voltages at frequencies appropriate for the desired tissue effect. The output of this stage is an AC waveform that can be controlled to voltage, current, or power, to deliver the correct energy to tissue.

A common technique for configuring a variable DC power supply utilizes Phase Shifted Full Bridge topology wherein output power is controlled via changes in the duty cycle of a pulse-width modulated input signal. At any single operating point, the gain of a phase shifted full-wave bridge inverter is linear. However, the operating points may vary over a wide range due to a setpoint change, a load change, an impedance change, and changes in other parameters. Consequently, the overall gain of the inverter stage can vary significantly. This can have an impact on the controlled delivery of energy to tissue.

SUMMARY

Disclosed is a system for controlling an electrosurgical generator using a gain-compensated full bridge topology. In embodiments, the disclosed system includes a summation unit configured to receive an RF setpoint signal and a calculated output signal, and to generate a first error signal corresponding to the difference between the RF setpoint signal and the calculated output signal. An impedance gain compensation unit in operable communication with the summation unit is configured to receive the first error signal and an impedance signal corresponding to the load impedance, and to generate a second error signal in accordance with an impedance correction calculation. A compensator in operable communication with the impedance gain compensation unit receives the second error signal and generates a phase control signal. In embodiments, the compensator includes a proportional-integral-derivative (PID) controller.

The system includes a phase gain compensation unit having a phase preprocessing module that is configured to receive the phase control signal, apply a phase gain correction function to the phase control signal to generate a corrected pulse width modulation driving signal. The phase gain compensation unit includes a pulse width modulation driver configured to generate a first full bridge driving signal and a second full bridge driving signal. The second full bridge driving signal is shifted in phase from the first full bridge driving signal by an amount corresponding to the corrected pulse width modulation driving signal. A full bridge inverter in operable communication with the pulse width modulation driver receives the first full bridge driving signal and the second full bridge driving signal, and generates an electrosurgical output signal having an electrical property corresponding to a difference in phase between the first full bridge driving signal and the second full bridge driving signal. The system includes a sensor circuit configured to sense an electrical property of the electrosurgical output signal and generate a corresponding calculated output signal. The electrical property may include, without limitation, an output voltage, an output current, an output power, or an output impedance.

In embodiments, the phase control circuit includes a clock configured to generate the first full bridge driving signal. The clock is disposed in operative communication with at least one of the pulse width modulation driver and the full-bridge inverter.

In embodiments, the sensor circuit includes one or more sensors operably associated with an output of the full-bridge inverter and configured to output a sensor signal having a first format. The sensor circuit includes a sensor unit in operable communication with the one or more sensors and configured to receive the sensor signal, convert the sensor signal from the first format into a second format, and outputting the sensor signal in the second format. In embodiments, the first format may be an analog format and the second format may be a digital format. A parameter calculation unit is configured to receive the sensor signal in the second format, and compute a calculated output signal in accordance with an operating mode of the electrosurgical generator. In embodiments, the operating mode of the electrosurgical generator is selected from the group consisting of a voltage-targeted mode, a current-targeted mode, a power-targeted mode, and an impedance-targeted mode.

In embodiments, the full bridge inverter includes a resonant network configured to provide a generally sinusoidal electrosurgical output waveform. In embodiments, the resonant network includes a bandpass filter.

In embodiments, the phase gain correction function is performed in accordance with an arcsine function.

In embodiments, the steady state output of a full bridge inverter in a voltage-targeted mode in accordance with the present disclosure, wherein a phase shifted square wave is well-filtered over a band pass network such that the Fourier fundamental is the dominant harmonic, may be determined in accordance with the formula $$|V_{out}| = \frac{4V_g}{\pi}\sin\frac{\theta_{12}}{2} * |H_v|,$$

where $H_v$ is the voltage transfer function of the resonant tank in combination with the load.

In embodiments, the steady state output of a full bridge inverter in a current-targeted mode in accordance with the present disclosure, wherein a phase shifted square wave is well-filtered over a band pass network such that the Fourier fundamental is the dominant harmonic, may be determined in accordance with the formula $$|I_{out}| = \frac{4V_g}{\pi}\sin\frac{\theta_{12}}{2} * \frac{|H_v|}{R_{LOAD}}.$$

In embodiments, the steady state output of a full bridge inverter in a power-targeted mode in accordance with the present disclosure, wherein a phase shifted square wave is well-filtered over a band pass network such that the Fourier fundamental is the dominant harmonic, may be determined in accordance with the formula $$|P_{out}| = \frac{\left(\frac{4V_g}{\pi}\sin\frac{\theta_{12}}{2} * |H_v|\right)^2}{R_{LOAD}}.$$

In embodiments, when the electrosurgical generator is in a current-targeted operating mode the impedance correction calculation is performed in accordance with the formula $$\text{abs}\left(\frac{R_{LOAD} + Z_{o0}}{1}\right).$$

In embodiments, when the electrosurgical generator is in a power-targeted operating mode the impedance correction calculation is performed in accordance with the formula $$\text{abs}\left(\frac{(R_{LOAD} + Z_{o0})^2}{R_{LOAD}}\right).$$

In embodiments, when the electrosurgical generator is in a voltage-targeted operating mode the impedance correction calculation is performed in accordance with the formula $$\text{abs}\left(\frac{R_{LOAD} + Z_{o0}}{R_{LOAD}}\right),$$

where $Z_{o0}$ is the Thevenin equivalent output impedance of the resonant network (e.g., reactive).

Also disclosed is a method for performing gain compensation in an electrosurgical generator. The method includes the steps of receiving an RF setpoint signal and a calculated output signal, generating a first error signal corresponding to the difference between the RF setpoint signal and the calculated output signal, generating a second error signal by applying an impedance correction calculation to the first error signal, generating a phase control signal with a proportional-integral-derivative controller, applying a phase gain correction function to the phase control signal to generate a corrected pulse width modulation driving signal, generating a first full bridge driving signal, and generating a second full bridge driving signal that is shifted in phase from the first full bridge driving signal by an amount corresponding to the corrected pulse width modulation driving signal.

In embodiments, the phase gain correction function is performed in accordance with an arcsine function.

In embodiments, the phase gain correction function is performed in accordance with an arcsine function when controlling to voltage or current.

In embodiments, the phase gain correction function is performed by squaring the compensator output and subsequently employing an arcsine function when controlling to power.

In embodiments, the disclosed method includes the steps of generating an electrosurgical output signal having an electrical property corresponding to a difference in phase between the first full bridge driving signal and the second full bridge driving signal. In embodiments, the disclosed method includes sensing an electrical property of the electrosurgical output signal and generating a calculated output signal corresponding to the electrosurgical output signal. In embodiments, the disclosed method includes converting the sensed electrical property from a first format into a second format. In embodiments, the calculated output signal is generated in accordance with an operating mode of the electrosurgical generator.

In embodiments of the disclosed method, when the electrosurgical generator is in a voltage-targeted mode the impedance correction calculation is performed in accordance with the formula $$\text{abs}\left(\frac{R_{LOAD} + Z_{o0}}{R_{LOAD}}\right),$$

where $Z_{o0}$ is the Thevenin equivalent output impedance of the resonant network and is reactive.

In embodiments of the disclosed method, when the electrosurgical generator is in a current-targeted mode the impedance correction calculation is performed in accordance with the formula $$\text{abs}\left(\frac{R_{LOAD} + Z_{o0}}{1}\right).$$

In embodiments of the disclosed method, when the electrosurgical generator is in a power-targeted mode the impedance correction calculation is performed in accordance with the formula $$\text{abs}\left(\frac{(R_{LOAD} + Z_{o0})^2}{R_{LOAD}}\right).$$

Also disclosed is an electrosurgical generator. In embodiments, the electrosurgical generator includes a controller configured to receive an operational parameter from a user interface, a user interface in operable communication with the controller and configured to receive a user input from a user, and a gain-compensated radiofrequency stage. The gain-compensated radiofrequency stage includes a summation unit configured to receive an RF setpoint signal and a calculated output signal, and to generate a first error signal corresponding to the difference between the RF setpoint signal and the calculated output signal. The gain-compensated inverter stage includes an impedance gain compensation unit configured to receive the first error signal and an impedance signal corresponding to the load impedance, and to generate a second error signal in accordance with an impedance correction calculation. The gain-compensated radiofrequency stage includes a compensator which receives the second error signal and generates a phase control signal. In embodiments, the compensator includes a proportional-integral-derivative controller.

The gain-compensated inverter stage includes a phase gain compensation unit. The phase gain compensation unit includes a phase preprocessing module that is configured to receive the phase control signal, apply phase change correction function to the phase control signal to generate a corrected pulse width modulation driving signal. The phase gain compensation unit further includes a pulse width modulation driver configured to generate a first full bridge driving signal, and a second full bridge driving signal that is shifted in phase from the first full bridge driving signal by an amount corresponding to the corrected pulse width modulation driving signal.

The inverter stage includes a full bridge inverter and a resonant network configured to receive the first full bridge driving signal and the second full bridge driving signal, and generate an electrosurgical output signal having an electrical property corresponding to the difference in phase between the first full bridge driving signal and the second full bridge driving signal. The gain-compensated inverter stage includes a sensor circuit configured to sense an electrical property of the electrosurgical output signal and generate a corresponding calculated output signal. The electrical property may include, without limitation, an output voltage, an output current, an output power, or an output impedance.

In embodiments, the sensor circuit of the electrosurgical generator includes one or more sensors operably associated with an output of the full-bridge inverter and configured to output a sensor signal having a first format. The sensor circuit includes a sensor unit in operable communication with the one or more sensors and configured to receive the sensor signal, convert the sensor signal from the first format into a second format, and outputting the sensor signal in the second format. The sensor circuit includes a parameter calculation unit configured to receive the sensor signal in the second format and compute a calculated output signal in accordance with an operating mode of the electrosurgical generator.

In embodiments of the electrosurgical generator, the phase gain correction function is performed in accordance with an arcsine function.

In embodiments of the electrosurgical generator, the phase gain correction function is performed in accordance with an arcsine function when performing voltage and/or current compensation.

In embodiments of the electrosurgical generator, the phase gain correction function is performed by squaring the compensator output and subsequently employing an arcsine function when performing power compensation.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
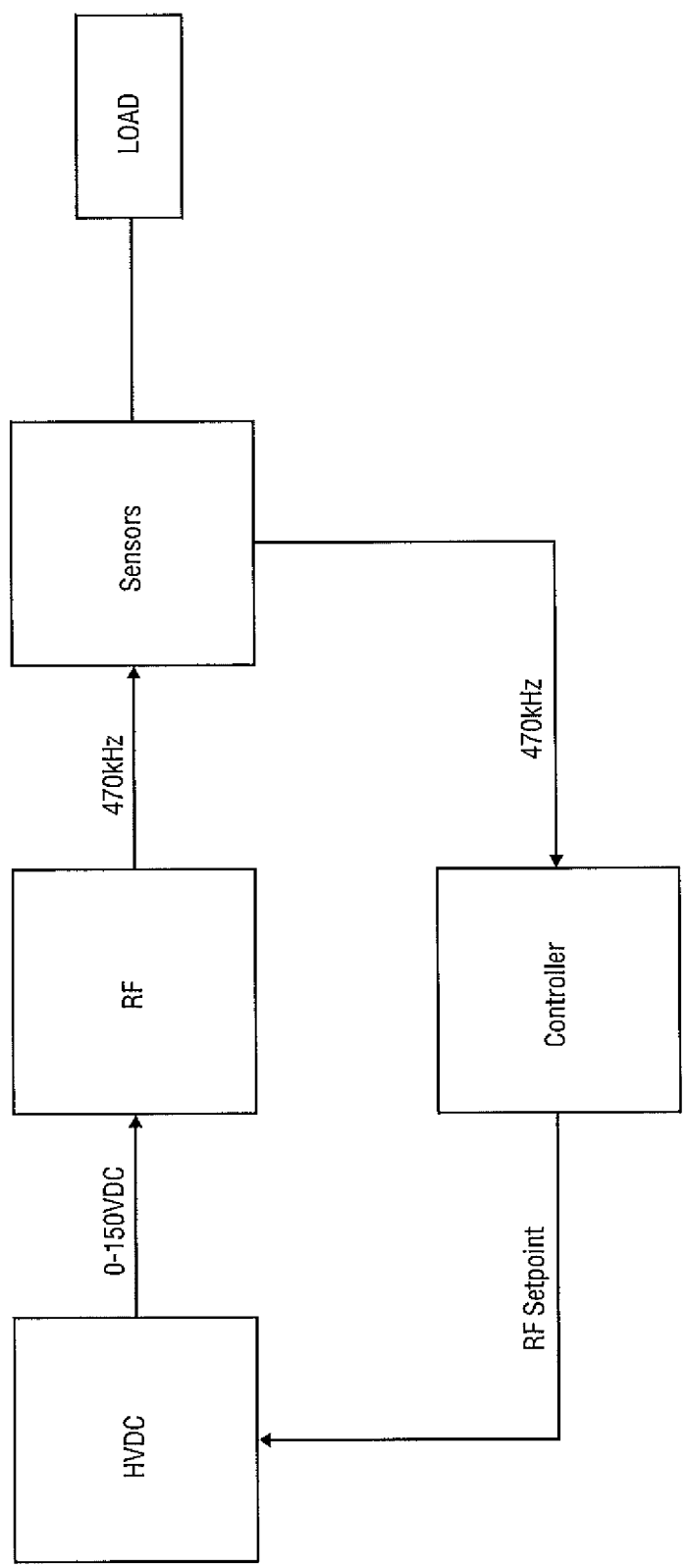
FIG. 1 is a block diagram of a prior-art electrosurgical generator.

Embodiments of the present disclosure are described herein below with reference to the accompanying drawings. In the following description, well-known functions or constructions are not described in detail to avoid obscuring the invention in unnecessary detail. In the Figures, like reference numerals represent like elements.

Additionally, embodiment in accordance with the present disclosure may be described herein in terms of functional block components and various processing steps. It should be appreciated that such functional blocks may be realized by any number of hardware and/or software components configured to perform the specified functions. For example, embodiments of the present disclosure may employ various integrated circuit components, e.g., memory elements, processing elements, logic elements, and the like, which may carry out a variety of functions under the control of one or more microprocessors or other control devices. Accordingly, functional blocks of the block diagrams support combinations of manners for performing the specified functions, combinations of steps for performing the specified functions, and program instructions for performing the specified functions. It will also be understood that each functional block of the block diagrams, and combinations of functional blocks in the block diagrams, can be implemented by either special purpose hardware-based systems that perform the specified functions or steps, or suitable combinations of special purpose hardware and software instructions.

In a prior-art electrosurgical generator arrangement as shown in FIG. 1, a high voltage DC power source (HVDC) provides a supply voltage that is variable from 0-150 VDC to an RF generator stage in accordance with an RF setpoint signal. The RF generator stage generates a 470 kHz electrosurgical signal having an output power determined by the supply voltage. One or more sensors monitor the output of the RF generator as applied to a load, such as to targeted tissue of a patent. The sensors provide a feedback signal to a controller. The controller is programmed to cause the RF generator stage to generate a desired RF output signal in accordance with inputs received from a surgeon. The desired RF output signal may include particular power, waveform, and modulations selected to achieve a specific surgical objective such as cutting, sealing, coagulating, blending, and so forth. The controller processes the feedback signal in view of the desired RF output signal and turn provides the appropriate RF setpoint signal to the HVDC to achieve the desired output signal. This arrangement may have drawbacks, since the output of the RF stage may be non-linear with respect to the variable supply voltage input, and may also exhibit inefficiencies and instabilities at certain operating points.

Figure 2:
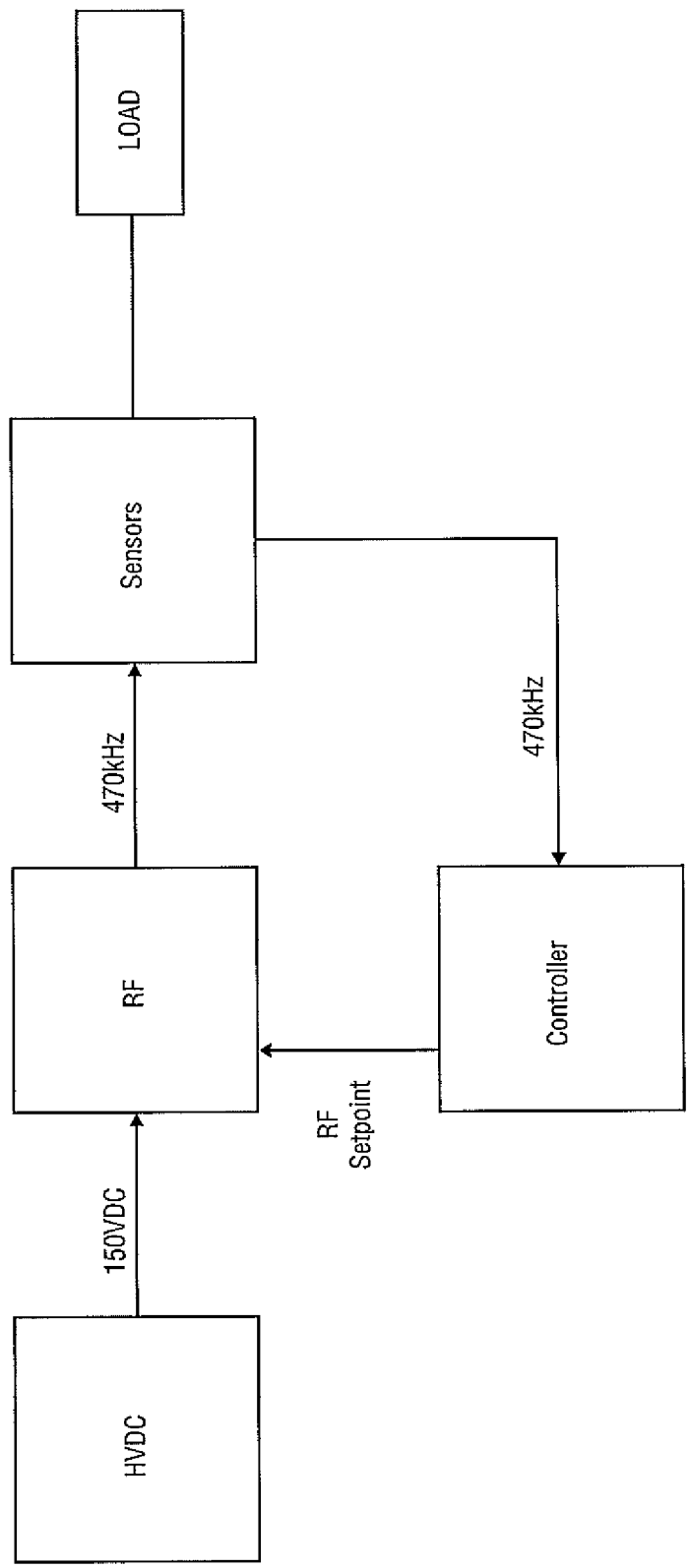
FIG. 2 is a block diagram of another prior-art electrosurgical generator.

In another prior-art electrosurgical generator arrangement shown in FIG. 2, an HVDC provides a fixed DC supply voltage of to the RF generator stage. The RF inverter is configured to operate at this fixed supply voltage and includes an RF setpoint input. The RF generator stage generates an high-frequency (e.g., 470 kHz) AC electrosurgical signal having an output determined by the RF setpoint input. This arrangement is said to have advantages over the FIG. 1 arrangement in that the system response time and operating efficiencies are improved.

Both the FIG. 1 and FIG. 2 arrangements may have drawbacks in that, as the operating point changes, either through a setpoint change or a load change, the gain exhibited by the system can vary significantly. Prior art solutions to the gain problem typically involve controlling a gain compensator based on known operating point data. A cross-reference of compensation factors and operating points is created by measuring the generator gain throughout an anticipated range of operating points and operation modes, which is then stored in a large three-dimensional lookup table for use during electrosurgical procedures. However, such approaches may have drawbacks, since the lookup tables are difficult to implement, are generally device-specific, and require extensive reprogramming if even a single element of the system is changed.

Figure 3A:
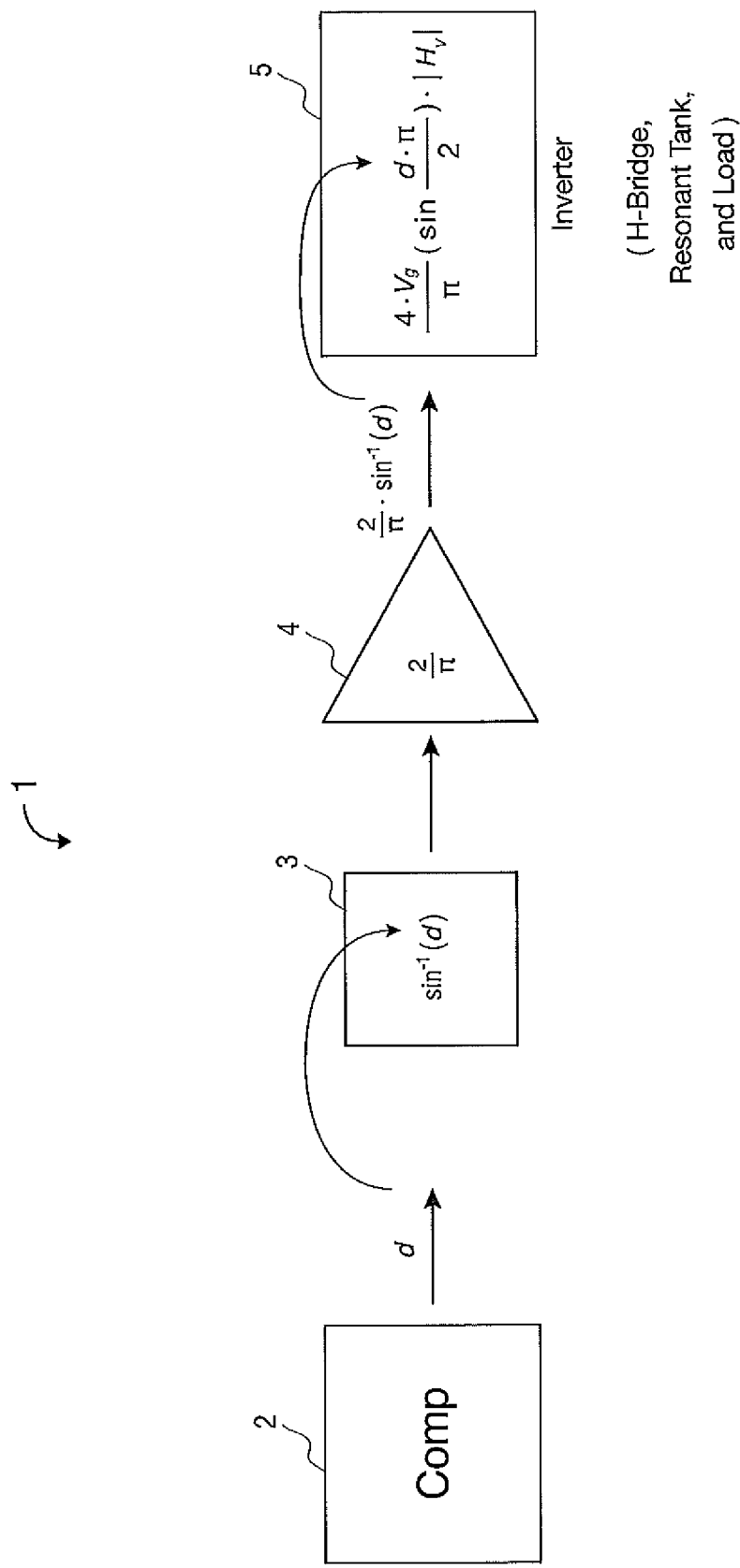
FIG. 3A is a network model of an electrosurgical generator in accordance with the present disclosure in voltage control mode and/or current control mode.

Turning to FIG. 3A, a network model of an electrosurgical generator 1 in accordance with the present disclosure in voltage control mode and/or current control mode is shown. In voltage control mode and current control mode, the variation due to phase is caused by the sine term. To correct for this variation, the phase gain correction function when controlling to voltage and/or current is performed in accordance with an arcsine function. Between the compensator 2 and the inverter 5, an arcsine block 3 and 2/π block 4 is placed. This is because the compensator is outputting duty cycle d (which ranges from 0 to 1) which would then be placed into the sine portion of the output voltage equation, as described in accordance with the formula $$\sin\frac{d \cdot \pi}{2},$$

with $d \cdot \pi = \theta_{12}$. The generator utilizes $$\frac{2}{\pi}\sin^{-1}(d)$$

as the d term of the sine function, which, in turn, results in a duty cycle of $$\sin\left(\frac{2}{pi} \cdot \frac{pi}{2}\sin^{-1}d\right) = d.$$

By this approach, the generator gain is constant with respect to phase in voltage and/or current mode, as the gain would be the derivative of d, not d itself.

Figure 3B:
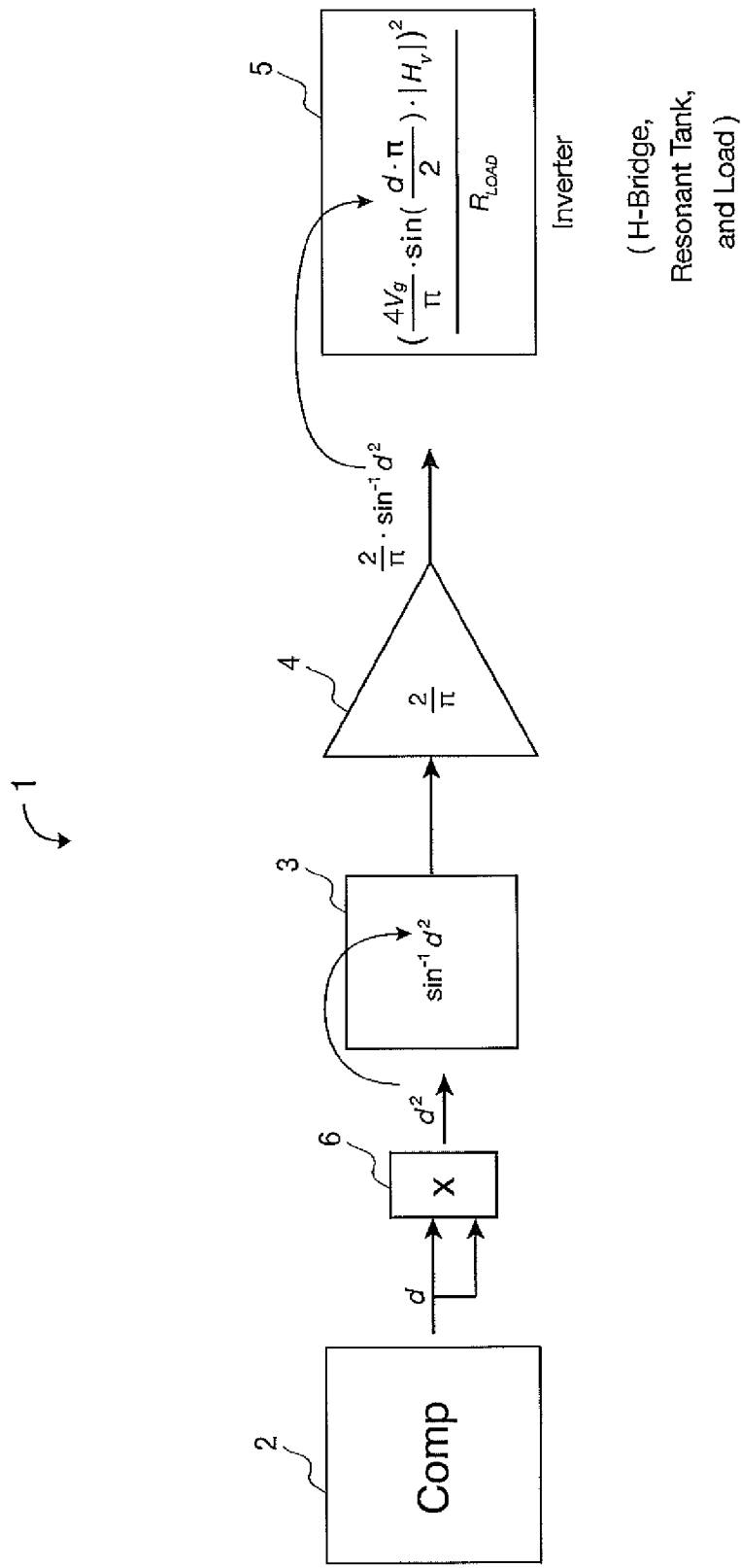
FIG. 3B is a network model of an electrosurgical generator in accordance with the present disclosure in power control mode.

Now with reference to FIG. 3B, a network model of an electrosurgical generator 1 in accordance with the present disclosure in power control mode is shown. In power control mode, the phase gain correction function is performed in accordance with the inverse of a sine squared function. In this model, between the compensator 2 and the arcsine block 3 a multiplier block 6 is placed which computer the square of uncorrected duty cycle d. In turn, the generator utilizes $$\frac{2}{\pi}\sin^{-1}(d^2)$$

as the d term of the sine squared function resulting in a corrected duty cycle of $$\sin^2\left(\frac{2}{pi} \cdot \frac{pi}{2} \cdot \sin^{-1}d^2\right) = d.$$

Again, by this approach the generator gain is constant with respect to phase.

Figure 4:
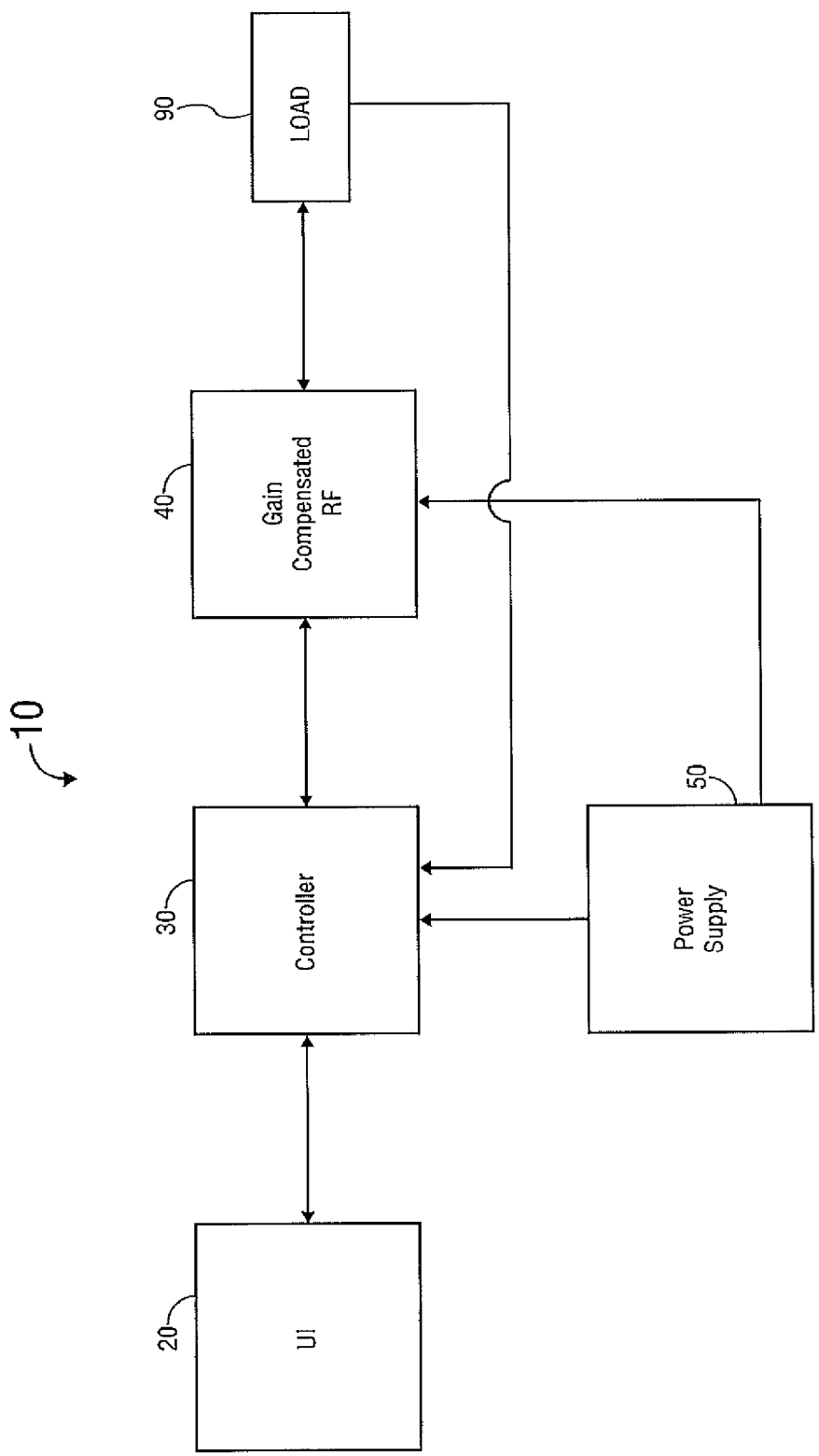
FIG. 4 is a block diagram of an embodiment of a gain-compensated electrosurgical generator in accordance with the present disclosure.

Referring now to FIG. 4, an electrosurgical generator 10 according to the present disclosure is illustrated. In general, the disclosed generator 10 compensates for the underlying cause of gain variations and precisely corrects the variation at the source. By normalizing the gain to a single point that applies across all conditions, not only is stability assured, but the overall control system design is greatly simplified. The described gain compensation technique is applicable any application utilizing phase shifted full bridge inverter topology. It is simpler than techniques that exist in the prior art and provides a generalized solution that will work across all circuits of this type.

The disclosed generator 10 includes a user interface 20 that is configured to receive inputs from a user that define the operating modes and parameters of the system such as, without limitation, power level, mono- or bi-polar mode, electrosurgical energy on/off, cutting mode, sealing mode, blending mode, coagulation mode, crest factor, and so forth. User interface 20 may include user interface elements such as buttons, knobs, keypads, touchscreens etc. that may be disposed on a generator enclosure and/or on an electrosurgical instrument. User interface 20 may include visual displays and audible indicators to communicate operating status and feedback to a user. Electrosurgical system 10 includes a controller 30 that is in operable communication with user interface 20 and a gain-compensated radiofrequency (RF) stage 40. Controller 30 interprets operating commands received from user interface 20 and, in turn, provides one or more control signals to gain-compensated RF stage 40, such as, without limitation, a setpoint signal. Gain-compensated RF stage 40 may be configured to communicate one or more operating parameters to controller 30, such as, without limitation, an impedance, an output voltage, an output current, and an output power. Gain-compensated RF stage 40 is configured to receive a setpoint signal from controller 30 and, in response thereto, generate an electrosurgical output signal for delivery to a load 90 (e.g., to targeted tissue) in a manner described in detail below. Electrosurgical generator 10 includes a power supply 50 which is configured to convert line voltage (e.g., 120 VAC or 240 VAC) to operating voltages required by user interface 20, controller 30, and gain-compensated RF stage 40. In some embodiments, power supply 50 is configured to provide +5 VDC, −5 VDC, +12 VDC, and +150 VDC.

Figure 5:
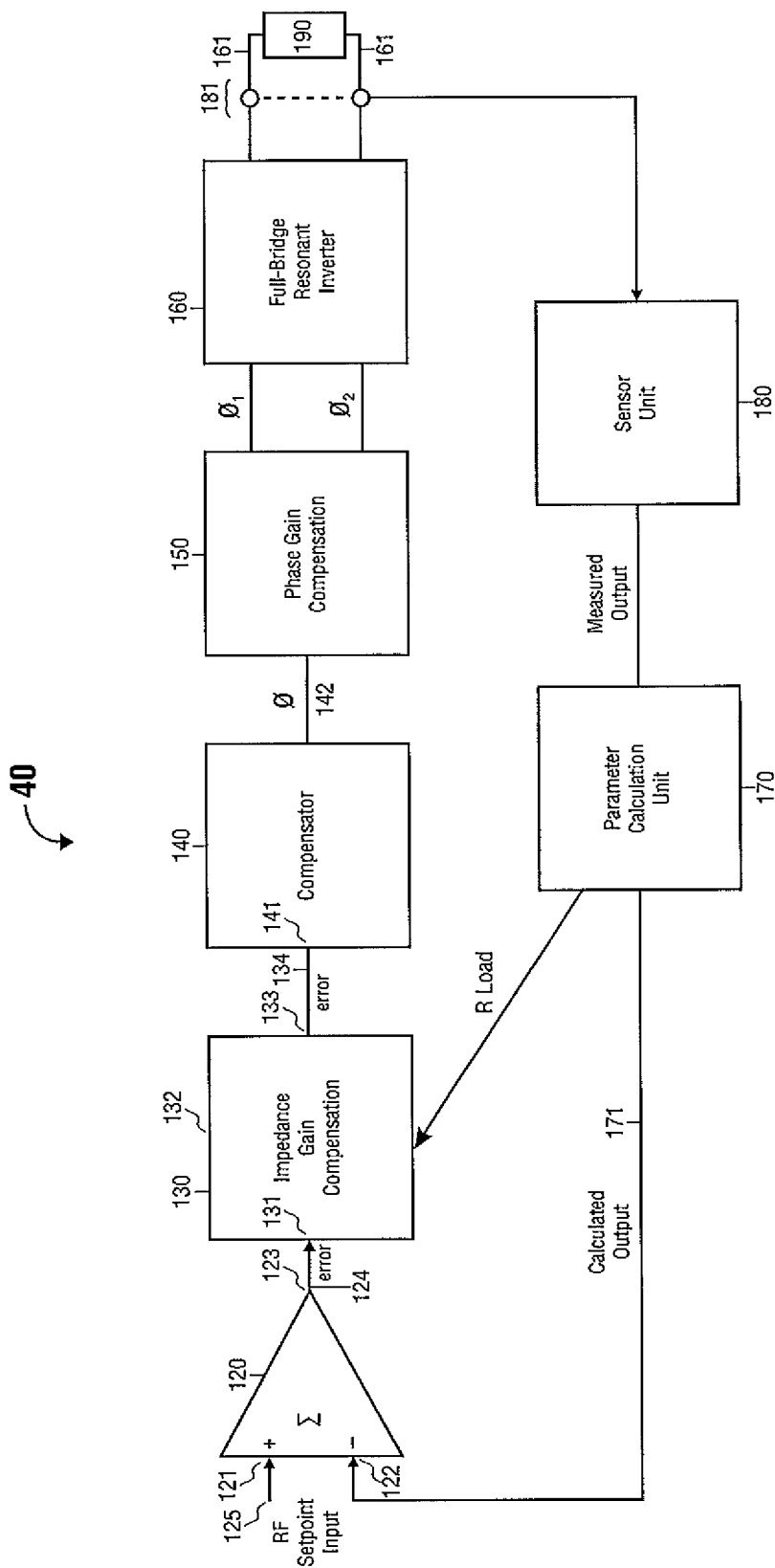
FIG. 5 is a block diagram of an embodiment of a gain-compensated RF stage of an electrosurgical generator in accordance with the present disclosure.
Figure 6:
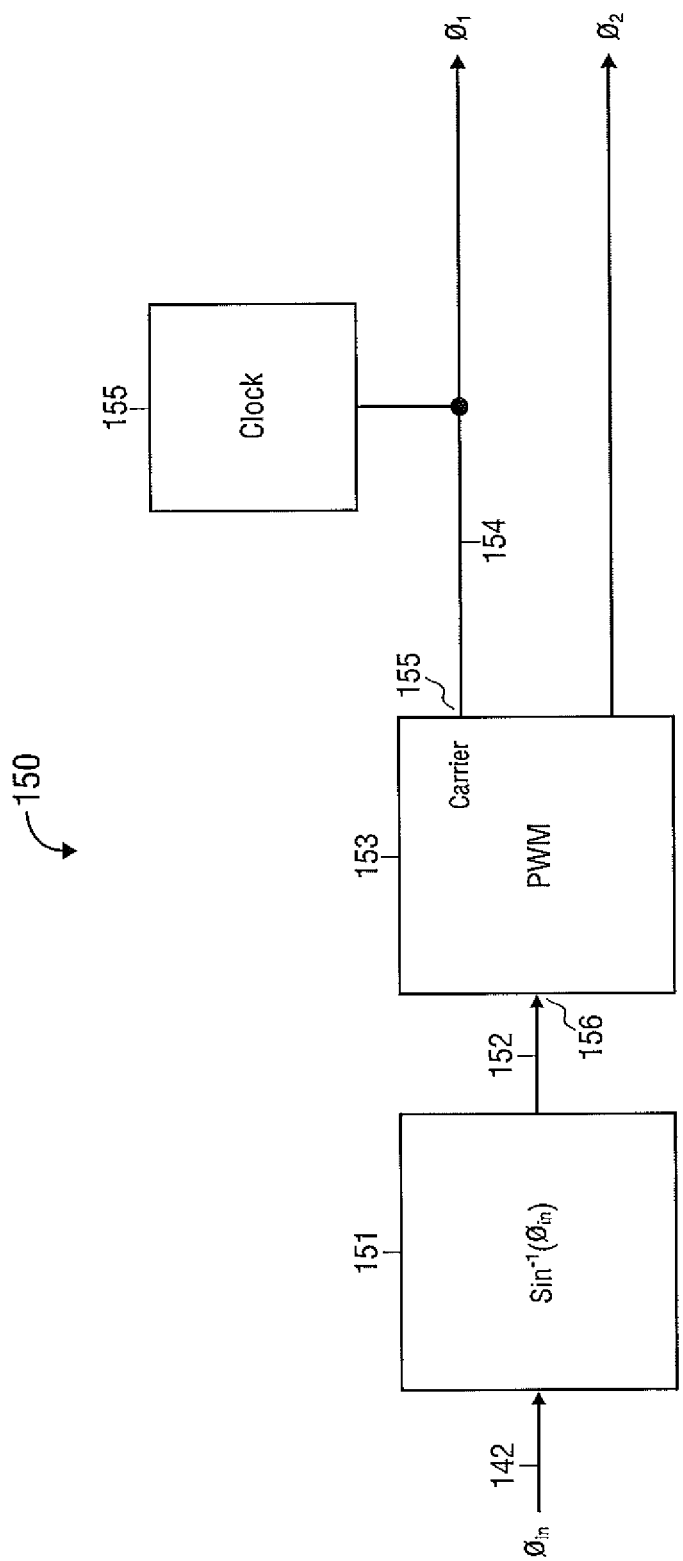
FIG. 6 is a block diagram of a phase gain compensation unit of an electrosurgical generator in accordance with the present disclosure.
Figure 7:
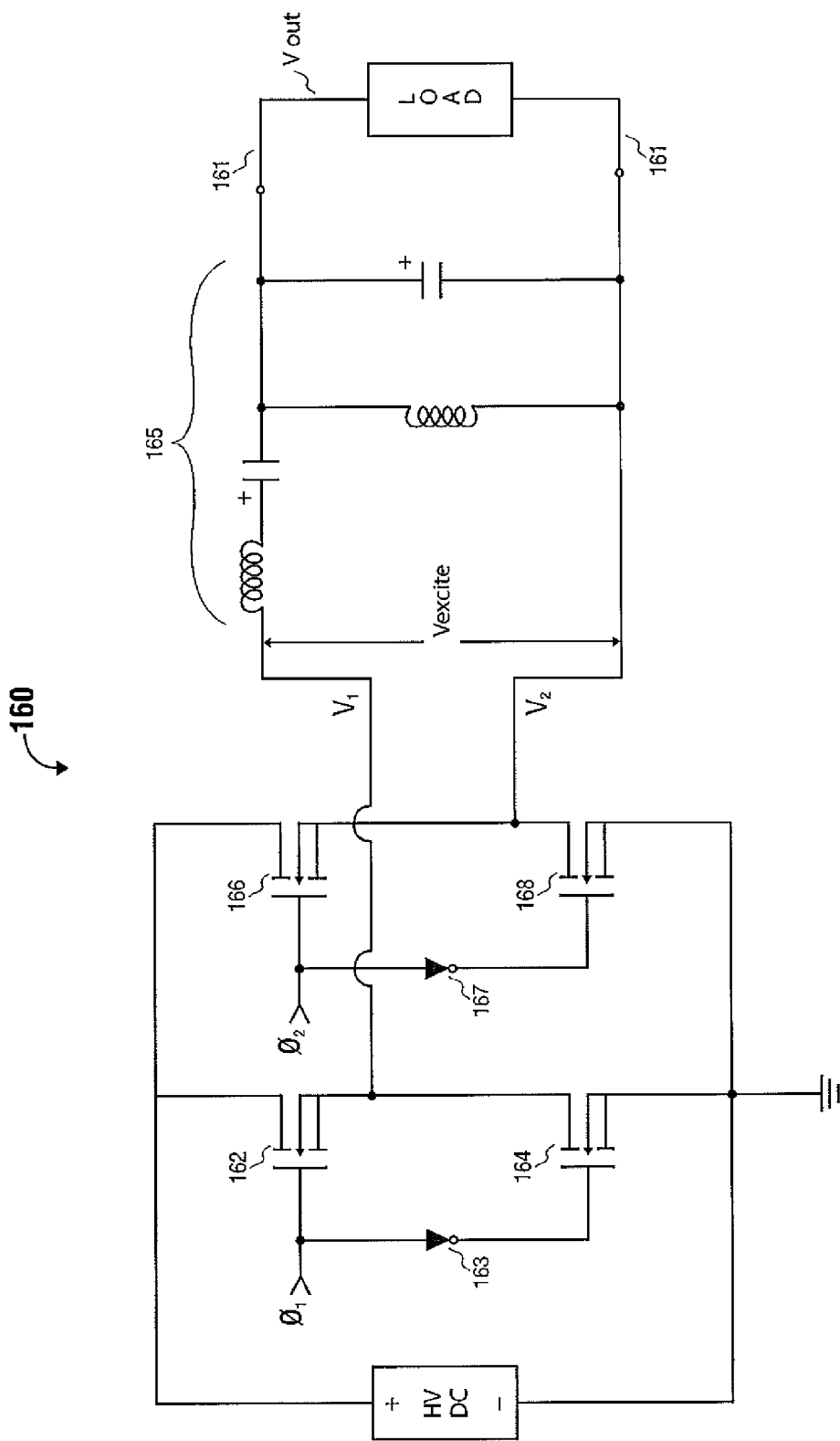
FIG. 7 is a schematic diagram of a full-bridge inverter output stage of an electrosurgical generator in accordance with the present disclosure.
Figure 8A:
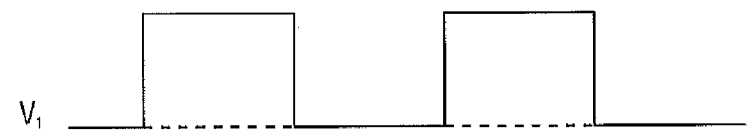
FIGS. 8A-8D illustrate relationships between operating waveforms of a full wave bridge inverter, shown at varying output levels, in accordance with an embodiment of the present disclosure.
Figure 8A:
Figure 8B:
Figure 8B:
Figure 8C:
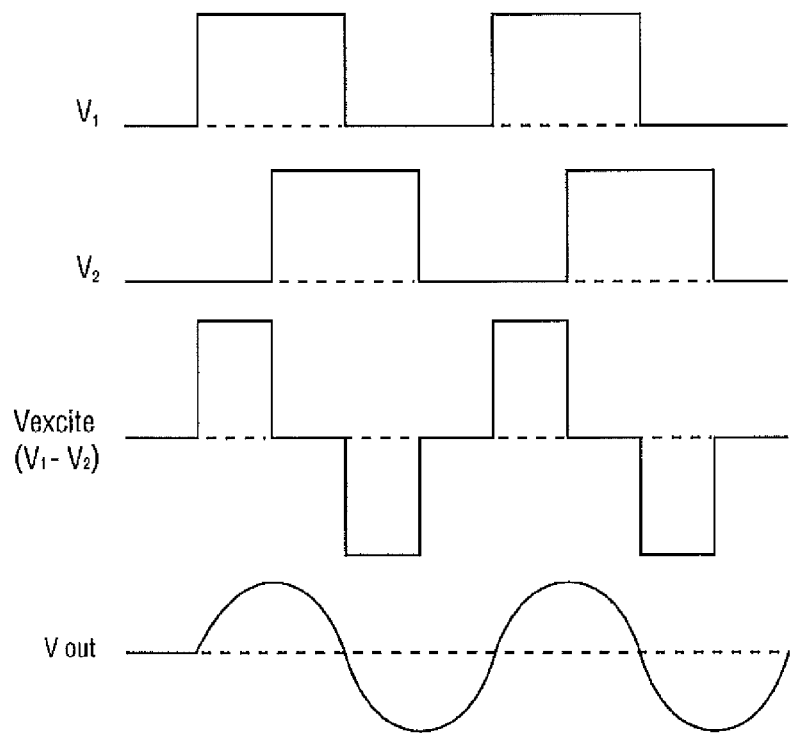
Figure 8D:
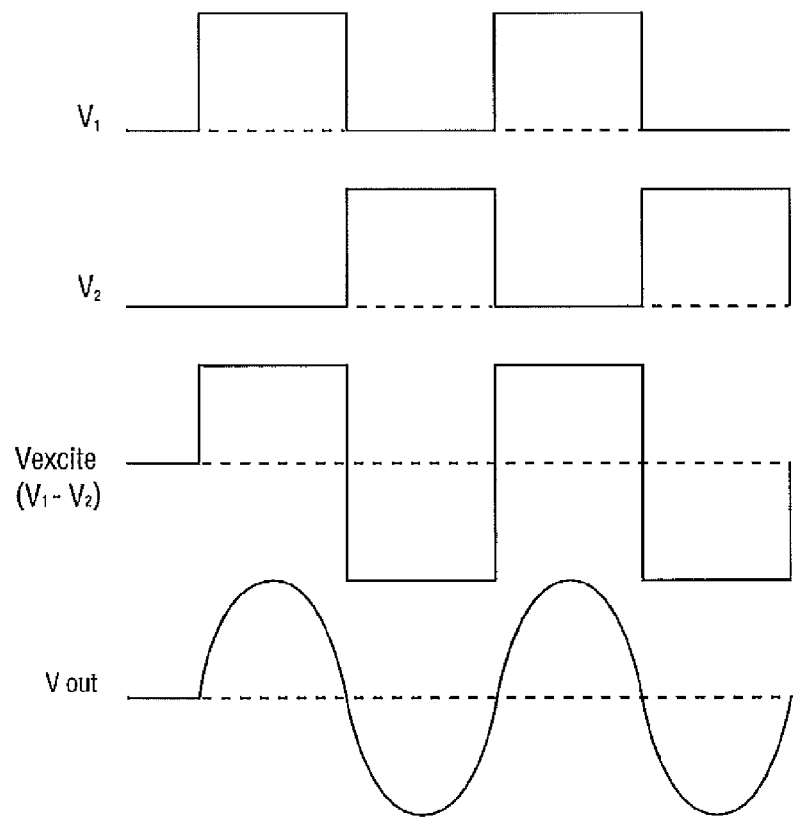

Turning now to FIGS. 5 and 6, a gain-compensated RF stage 40 in accordance with the present disclosure is now described. Gain-compensated RF stage 40 employs a two-part approach to achieving gain compensation. The first approach addresses gain variations caused by load (impedance) variations of a full-bridge resonant inverter output stage 160. The second approach addresses gain variation caused by the sine term of the duty cycle modulation (e.g., pulse width modulation) of the full-bridge resonant inverter output stage 160 during current- and voltage-control modes, and gain variation caused by the sine squared term of the duty cycle modulation during power control modes.

In greater detail, gain-compensated RF stage 40 is generally arranged as an improved control loop having two gain-compensation error-correction elements. A first impedance gain compensation unit 130 is provided prior to the input of a PID section 140, and a phase gain compensation unit 150 is provided subsequent to the PID section 140. Gain-compensated RF stage 40 includes a summation amplifier 120 having an RF setpoint input 121 which receives RF setpoint signal 125 at a positive (+) input of summation amplifier 120. A calculated output signal 171 (e.g., a setpoint "equivalent" corresponding to an output parameter) is received at a negative (−) input of summation amplifier 120. Summation amplifier 120 generates a first error signal 124 at summation amplifier output 123 corresponding to the difference between the RF setpoint signal 125 (e.g., desired output) and the calculated output signal 171 (e.g., actual output). The first error signal 124 which is communicated as the error term to an error input 131 of impedance gain compensation unit 130. In addition to error input 131, impedance gain compensation unit 130 includes load input 132 that is configured to receive a load signal $R_{LOAD}$ from full-bridge resonant inverter 160. As such, impedance gain compensation unit 130 is configured to compensate for load variations of full-bridge resonant inverter 160 in addition to gain variations.

Impedance gain compensation unit 130 is configured to generate second error signal 134 at impedance gain compensation unit output 133 that is communicated to PID controller 140. The compensation required due to load variation is dependent not only on the load, but also on the control method. However, because tissue impedance changes relatively slowly in comparison to the frequency at which the setpoint may be changed, gain compensation based on load is reliably achieved. The load compensation is determined in accordance the gain variation equations listed in Table 1, presented below, wherein Zo0 is the Thevenin equivalent output impedance of the resonant network (e.g., reactive):

TABLE 1

| Voltage | Current | Power |
|---|---|---|
| $\text{abs}\left(\dfrac{R_{LOAD}}{R_{LOAD} + Z_{o0}}\right)$ | $\text{abs}\left(\dfrac{1}{R_{LOAD} + Z_{o0}}\right)$ | $\text{abs}\left(\dfrac{R_{LOAD}}{(R_{LOAD} + Z_{o0})^2}\right)$ |

The reciprocals of the gain variations calculated by the equations of Table 1 generate the error term to be applied to error input 141 of PID controller 140, to effectively normalize the gain due to impedance. The gain compensation equations are presented below in Table 2:

TABLE 2

| Voltage | Current | Power |
|---|---|---|
| $\text{abs}\left(\dfrac{R_{LOAD} + Z_{o0}}{R_{LOAD}}\right)$ | $\text{abs}\left(\dfrac{R_{LOAD} + Z_{o0}}{1}\right)$ | $\text{abs}\left(\dfrac{(R_{LOAD} + Z_{o0})^2}{R_{LOAD}}\right)$ |

Impedance gain compensation unit 130 is programmed to receive the load as a parameter, and adds or removes gain from the system prior to processing by phase gain compensator 150 by preprocessing (e.g., pre-distorting) the error term of the inner control loop in order to compensate for the gain non-linearity due to impedance changes.

PID unit 140 receives error signal 134 from impedance gain compensation unit 130 and generates a phase control signal 142 which determines the duty cycle of a full-bridge inverter driver, e.g., a pulse width modulation unit, included within phase gain compensation unit 150.

With attention now to FIG. 6, phase gain compensation unit 150 receives phase control signal 142. The phase gain compensation unit 150 corrects for the inherent nonlinearity associated with pulse width modulation techniques. In more detail, in prior-art full bridge inverters, a linear increase of the pulse width modulation duty cycle results in an increase in full-bridge inverter peak-to-peak output in accordance with the sine term. For example, varying the PWM duty cycle (by, e.g., varying the phase difference between the two pulse trains) from 0% to 50% results in the output of a full-bridge inverter (to vary from 0% to 70.7% of peak value.

To compensate for this nonlinearity, in embodiments according to the present disclosure the phase gain compensation unit 150 compensates (e.g., pre-processes or pre-distorts) phase control signal 142 by applying a compensation factor that is based at least in part upon the arcsine term to phase control signal 142, which, in turn, generates a corrected PWM driving signal 152. Phase control signal 142 is received by phase preprocessing module 151. Phase preprocessing module 151 applies the arcsine term to phase control signal 142 to generate PWM driving signal 152. A clock 155 provides a square wave 154 having a phase θ1 to a carrier input 155 of PWM driver 153. In embodiments, clock 155 may be integral to and/or included within PWM driver 153. Typically, square wave 154 has a frequency corresponding to the desired electrosurgical frequency, e.g., 470 kHz. The corrected PWM driving signal 152 is applied to a modulation input 156 of PWM driver 153, which generates a phase-shifted, second square wave having a phase θ2. The phase difference between θ1 and θ2 is determined by PWM driving signal 152. Phase θ1 and phase θ2 are output from phase gain compensation unit 150 to drive full-bridge inverter 160. Thus, the phase difference between θ1 and θ2 is pre-processed by the arcsine function by phase preprocessing module 151, which precisely compensates for the sine term nonlinearity of the full bridge inverter 160. In this manner, a purely linear response to the PID 140 output is achieved.

Referring to FIGS. 7 and 8A-8D, full-bridge inverter 160 is now described in more detail. The full-bridge inverter 160 includes a plurality of transistors 162, 164, 166, 168 for configured in a full bridge arrangement to generate a pair of output pulse trains $V_1$, $V_2$. Full-bridge inverter 160 receives phase θ1 and phase θ2 outputs from phase gain compensation unit 150 for driving the plurality of transistors 162, 164, 166, 168. The PWM output is coupled to transistor 162, and, shifted 180 degrees by inverter 163, to transistor 164. Similarly, θ2 is coupled to transistor 166, and to transistor 168 via inverter 167. This push-pull topology is used to accomplish voltage conversion from DC to RF at a desired power level determined by the phase difference between phase θ1 and phase θ2.

As the phase difference between PWM drive signals phase θ1 and phase θ2 is varied, the transistor pairs 162, 164 and 166, 168 conduct in accordance with their respective gate signals, at varying times, to deliver a waveform at the specified power. As best shown in FIGS. 7A-7D, the interference between the two phase shifted, high voltage pulse-trains $V_1$ and $V_2$ generates a combined excitation voltage $V_{EXCITE}$. $V_1$ and $V_2$ are thus summed and subsequently filtered by resonant network 165 to provide a smoothed, generally sinusoidal electrosurgical output waveform 161, 161' ($V_{out}$).

One or more sensors 181 are operably associated with outputs 161, 161' and/or load 190. In embodiments, sensor 181 includes a voltage sensor and/or a current sensor. One or more sensor signals from sensor 181 are received at sensor unit 180, which interfaces and converts the raw sensors signals received from sensor 181 into a format suitable for use by parameter calculation unit 170. In embodiments, sensor unit 180 may include an analog to digital (A/D) converter, a buffer, an optoisolator, an amplifier, a temperature compensation device, a filter, and combinations thereof.

Parameter calculation unit 170 receives the one or more sensor signals, and computes a calculated output signal 171 (i.e., a setpoint equivalent parameter) corresponding to the presently-sensed output of full-bridge inverter 160. The calculated output signal 171 is calculated in accordance with a current operating mode of the generator 10. For example, RMS voltage, RMS current, average power, and impedance may be calculated. If the control method of generator 10 is in a voltage-targeted mode, then the present output voltage is calculated by parameter calculation unit and subtracted from the setpoint by summation amplifier 120. If the control method of generator 10 is in a voltage-targeted mode, then the calculated output signal 171 is calculated from the present output voltage. If the control method of generator 10 is in a current-targeted mode, the calculated output signal 171 is calculated from the present output current. Similarly, if the control method of generator 10 is in a power-targeted mode, then present output power is calculated, and if the control method of generator 10 is in an impedance-targeted mode, then the present load impedance is calculated. The calculated output signal 171 is received at the negative (−) input of summation amplifier 120, which sums the setpoint signal 125 with the calculated output signal 171, to generate the error signal 124 used to drive the gain-compensated RF stage 40 as just described.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A system for controlling an electrosurgical generator using a gain-compensated full bridge topology, comprising:
   a summation unit configured to receive a radiofrequency (RF) setpoint signal and a calculated output signal, and to generate a first error signal corresponding to a difference between the RF setpoint signal and the calculated output signal;
   an impedance gain compensation unit configured to receive the first error signal and an impedance signal corresponding to a load impedance, and to generate a second error signal by applying an impedance correction calculation to the first error signal;
   a controller configured to receive the second error signal and to generate a phase control signal;
   a phase gain compensation unit, comprising:
      a phase preprocessing module that is configured to receive the phase control signal and apply a phase gain correction function to the phase control signal to generate a corrected pulse width modulation driving signal; and
      a pulse width modulation driver configured to generate a first full bridge driving signal and a second full bridge driving signal that is shifted in phase from the first full bridge driving signal by an amount corresponding to the corrected pulse width modulation driving signal;
   a full bridge inverter configured to receive the first full bridge driving signal and the second full bridge driving signal and generate an electrosurgical output signal having an electrical property corresponding to a difference in phase between the first full bridge driving signal and the second full bridge driving signal; and
   a sensor circuit configured to sense an electrical property of the electrosurgical output signal and generate a corresponding calculated output signal.

2. The system in accordance with claim 1, wherein the phase gain compensation unit includes a clock configured to generate the first full bridge driving signal and disposed in operative communication with at least one of the pulse width modulation driver and the full-bridge inverter.

3. The system in accordance with claim 1, wherein the sensor circuit comprises:

one or more sensors operably associated with an output of the full-bridge inverter and configured to output a sensor signal having a first format;

a sensor unit in operable communication with the one or more sensors and configured to receive the sensor signal, convert the sensor signal from the first format into a second format, and outputting the sensor signal in the second format; and a parameter calculation unit configured to receive the sensor signal in the second format and compute a calculated output signal in accordance with an operating mode of the electrosurgical generator.

4. The system in accordance with claim 3, wherein the operating mode of the electrosurgical generator is selected from the group consisting of a voltage-targeted mode, a current-targeted mode, a power-targeted mode, and an impedance-targeted mode.

5. The system in accordance with claim 1, wherein the full bridge inverter includes a resonant network configured to provide a generally sinusoidal electrosurgical output waveform.

6. The system in accordance with claim 1, wherein the phase gain correction function is performed in accordance with an arcsine function.

7. The system in accordance with claim 1, wherein the full bridge inverter includes a resonant network, and when the electrosurgical generator is in a voltage-targeted mode the impedance correction calculation is performed in accordance with the formula $$\text{abs}\left(\frac{R_{LOAD} + Z_{o0}}{R_{LOAD}}\right),$$

in which $Z_{o0}$ is a Thevenin equivalent output impedance of the resonant network and $R_{LOAD}$ is a load signal received from the full bridge inverter.

8. The system in accordance with claim 1, wherein the full bridge inverter includes a resonant network, and wherein when the electrosurgical generator is in a current-targeted mode the impedance correction calculation is performed in accordance with the formula $$\text{abs}\left(\frac{R_{LOAD} + Z_{o0}}{1}\right),$$

in which $Z_{o0}$ is a Thevenin equivalent output impedance of the full bridge inverter and $R_{LOAD}$ is a load signal received from the full bridge inverter.

9. The system in accordance with claim 1, wherein the full bridge inverter includes a resonant network, and when the electrosurgical generator is in a power-targeted mode the impedance correction calculation is performed in accordance with the formula $$\text{abs}\left(\frac{(R_{LOAD} + Z_{o0})^2}{R_{LOAD}}\right),$$

in which $Z_{o0}$ is a Thevenin equivalent output impedance of the full bridge inverter and $R_{LOAD}$ is a load signal received from the full bridge inverter.

10. A method for performing gain compensation in an electrosurgical generator, comprising:

receiving an RF setpoint signal and a calculated output signal;

generating a first error signal corresponding to a difference between the RF setpoint signal and the calculated output signal;

generating a second error signal by applying an impedance correction calculation to the first error signal;

generating, with a compensator, a phase control signal;

applying a phase gain correction function to the phase control signal to generate a corrected pulse width modulation driving signal;

generating a first full bridge driving signal; and generating a second full bridge driving signal that is shifted in phase from the first full bridge driving signal by an amount corresponding to the corrected pulse width modulation driving signal.

11. The method in accordance with claim 10, further comprising:

generating an electrosurgical output signal having an electrical property corresponding to a difference in phase between the first full bridge driving signal and the second full bridge driving signal.

12. The method in accordance with claim 11, further comprising:

sensing an electrical property of the electrosurgical output signal; and generating a calculated output signal corresponding to the electrosurgical output signal.

13. The method in accordance with claim 12, wherein the calculated output signal is generated in accordance with an operating mode of the electrosurgical generator.

14. The system in accordance with claim 10, wherein the phase gain correction function is performed in accordance with an arcsine function.

15. The method in accordance with claim 10, wherein when the electrosurgical generator is in a voltage-targeted mode the impedance correction calculation is performed in accordance with the formula $$\text{abs}\left(\frac{R_{LOAD} + Z_{o0}}{R_{LOAD}}\right),$$

in which $Z_{o0}$ is a Thevenin equivalent output impedance received from a resonant network of a full bridge inverter and $R_{LOAD}$ is a load signal received from the full bridge inverter.

16. The method in accordance with claim 10, wherein when the electrosurgical generator is in a current-targeted mode the impedance correction calculation is performed in accordance with the formula $$\text{abs}\left(\frac{R_{LOAD} + Z_{o0}}{1}\right),$$

in which $Z_{o0}$ is a Thevenin equivalent output impedance received from a resonant network of a full bridge inverter and $R_{LOAD}$ is a load signal received from the full bridge inverter.

17. The method in accordance with claim 10, wherein when the electrosurgical generator is in a power-targeted mode the impedance correction calculation is performed in accordance with the formula $$\text{abs}\left(\frac{(R_{LOAD} + Z_{o0})^2}{R_{LOAD}}\right),$$

in which $Z_{o0}$ is a Thevenin equivalent output impedance received from a resonant network of a full bridge inverter and $R_{LOAD}$ is a load signal received from the full bridge inverter.

18. An electrosurgical generator, comprising:
   a controller configured to receive an operational parameter from a user interface;
   a user interface in operable communication with the controller and configured to receive a user input from a user; and
   a gain-compensated radiofrequency stage, comprising:
      a summation unit configured to receive an RF setpoint signal and a calculated output signal, and to generate a first error signal corresponding to a difference between the RF setpoint signal and the calculated output signal;
      an impedance gain compensation unit configured to receive the first error signal and an impedance signal corresponding to a load impedance, and to generate a second error signal by applying an impedance correction calculation to the first error signal;
      a controller configured to receive the second error signal and to generate a phase control signal;
      a phase gain compensation unit, comprising:
         a phase preprocessing module that is configured to receive the phase control signal and apply phase change correction function to the phase control signal to generate a corrected pulse width modulation driving signal; and
         a pulse width modulation driver configured to generate a first full bridge driving signal and a second full bridge driving signal that is shifted in phase from the first full bridge driving signal by an amount corresponding to the corrected pulse width modulation driving signal;
      a full bridge inverter configured to receive the first full bridge driving signal and the second full bridge driving signal and generate an electrosurgical output signal having an electrical property corresponding to a difference in phase between the first full bridge driving signal and the second full bridge driving signal; and
      a sensor circuit configured to sense an electrical property of the electrosurgical output signal and generate a corresponding calculated output signal.

19. The electrosurgical generator in accordance with claim 18, wherein the sensor circuit comprises:
   one or more sensors operably associated with an output of the full-bridge inverter and configured to output a sensor signal having a first format;
   a sensor unit in operable communication with the one or more sensors and configured to receive the sensor signal, convert the sensor signal from the first format into a second format, and outputting the sensor signal in the second format; and
   a parameter calculation unit configured to receive the sensor signal in the second format and compute a calculated output signal in accordance with an operating mode of the electrosurgical generator.

20. The electrosurgical generator in accordance with claim 18, wherein the phase gain correction function is performed in accordance with an arcsine function.

* * * * *